US009244008B2

(12) United States Patent
Kang et al.

(10) Patent No.: US 9,244,008 B2
(45) Date of Patent: Jan. 26, 2016

(54) SURFACE PLASMON RESONANCE SENSOR ELEMENT AND SENSOR INCLUDING THE SAME

(75) Inventors: Myungchan Kang, Woodbury, MN (US); Bing Hao, Woodbury, MN (US); Brian K. Nelson, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 25 days.

(21) Appl. No.: 14/124,835

(22) PCT Filed: Jun. 13, 2012

(86) PCT No.: PCT/US2012/042233
§ 371 (c)(1),
(2), (4) Date: Dec. 9, 2013

(87) PCT Pub. No.: WO2012/174099
PCT Pub. Date: Dec. 20, 2012

(65) Prior Publication Data
US 2014/0111809 A1  Apr. 24, 2014

Related U.S. Application Data

(60) Provisional application No. 61/497,632, filed on Jun. 16, 2011.

(51) Int. Cl.
*G01N 21/55* (2014.01)
*G01N 21/47* (2006.01)
*G01N 21/552* (2014.01)

(52) U.S. Cl.
CPC .............. *G01N 21/47* (2013.01); *G01N 21/553* (2013.01)

(58) Field of Classification Search
CPC ...................... G01N 21/55; G01N 2021/5903
USPC ......................................................... 356/445
See application file for complete search history.

(56) References Cited

U.S. PATENT DOCUMENTS 7,193,711 B2 * 3/2007 Rassman et al. .............. 356/369
7,449,146 B2   11/2008 Rakow
(Continued)

FOREIGN PATENT DOCUMENTS

JP    06-281610    10/1994
JP    08-193948    7/1996
(Continued)

OTHER PUBLICATIONS

Budd "Polymers of intrinsic microporosity (PIMs): robust, solution-processable, organic nanoporous materials", Chemical Communications (Cambridge), Jan. 8, 2004, vol. 2004, No. 2, pp. 230-231. XP55036998.

(Continued)

*Primary Examiner* — Roy M Punnoose
(74) *Attorney, Agent, or Firm* — Yufeng Dong; Bradford B. Wright (57) ABSTRACT

A surface plasmon resonance sensor element includes a thin metallic layer, an optical construction disposed on the thin metallic layer for directing light to and away from the thin metallic layer, and an absorptive layer disposed on the thin metallic layer opposite the optical construction. The absorptive layer includes a polymer of intrinsic microporosity having an average pore volume of at least 0.4 cubic nanometers.

18 Claims, 2 Drawing Sheets

(56) References Cited

U.S. PATENT DOCUMENTS

| | | | |
|---|---|---|---|
| 7,715,002 B2* | 5/2010 | Popp et al. .................... | 356/300 |
| 7,767,143 B2 | 8/2010 | Wendland | |
| 8,409,511 B2 | 4/2013 | Thomas | |
| 8,576,400 B2 | 11/2013 | Hulteen | |
| 2003/0048452 A1* | 3/2003 | Johansen .................... | 356/445 |
| 2003/0174384 A1* | 9/2003 | Halas et al. .................. | 359/296 |
| 2006/0170927 A1* | 8/2006 | Wang et al. .................. | 356/445 |
| 2006/0246273 A1 | 11/2006 | Mckeown | |
| 2007/0140907 A1 | 6/2007 | Rakow | |
| 2010/0157306 A1 | 6/2010 | Choi | |
| 2010/0189600 A1 | 7/2010 | Hulteen | |
| 2011/0031983 A1 | 2/2011 | David | |
| 2011/0045601 A1 | 2/2011 | Gryska | |
| 2013/0119242 A1* | 5/2013 | Goddard et al. ......... | 250/227.14 |
| 2013/0186177 A1 | 7/2013 | Palazzotto | |

FOREIGN PATENT DOCUMENTS

| | | |
|---|---|---|
| WO | WO 2005-012397 | 2/2005 |
| WO | WO 2010-117599 | 10/2010 |

OTHER PUBLICATIONS

Budd, "Solution-Processed, Organophilic Membrane Derived from a Polymer of Intrinsic Microporosity", Advanced Materials, Mar. 2004, vol. 16, No. 5, pp. 456-459.XP55O37OOO.

Budd, "Gas separation membranes from polymers of intrinsic microporosity", Journal of Membrane Science, Apr. 2005, vol. 251, No. 1-2, pp. 263-269.

Busche, "Quantification of binary mixtures of the freones R22 and R134a by surface plasmon resonance", Sensors and Actuators B: Chemical, Mar. 2003, vol. 89, No. 1-2, pp. 192-198.

Capan, "Characterisation and vapour sensing properties of spin coated thin films of anthracene labelled PMMA polymer", Materials Science and Engineering: C, 2009, vol. 29, pp. 1114-1117.

Dlubek, "Positron Lifetime Studies of Free Volume Hole Size Distribution in Glassy Polycarbonate and Polystyrene", physica status solidi (a), Oct. 1996, vol. 157, No. 2, pp. 351-364.

Emmler, "Free Volume Investigation of Polymers of Intrinsic Microporosity (PIMs): PIM-1 and PIM1 Copolymers Incorporating Ethanoanthracene Units", Macromolecules, Jun. 2010, vol. 43, No. 14, pp. 6075-6084.

Kasper, "Quantification of Quaternary Mixtures of Alcohols: A Comparison of Reflectometric Interference Spectroscopy and Surface Plasmon Resonance Spectroscopy", Measurement Science and Technology, 2004, vol. 15, pp. 540-548.

Kieser "Discrimination of Methanol and Ethanol Vapors by the Use of a Single Optical Sensor with a Microporous Sensitive Layer", Analytical Chemistry, Sep. 2002, vol. 74, No. 18, pp. 4781-4787.

Kristiak, "Free-volume microstructure of amorphous polycarbonate at low temperatures determined by positron-annihilation-lifetime spectroscopy", Physical Review B, Mar. 1994, vol. 49, No. 10, pp. 6601-6607.

McKeown, "Exploitation of Intrinsic Microporosity in Polymer-Based Materials", Macromolecules, May 2010, vol. 43, No. 12, pp. 5163-5176.XP55037046.

McKeown, "Polymers of Intrinsic Microporosity (PIMs): Bridging the Void between Microporous and Polymeric Materials", Jan. 2005, vol. 11, No. 9, pp. 2610-2620.

Miranda, "Unusual temperature dependence of the positron lifetime in a polymer of intrinsic microporosity", physica status solidi (RRL), vol. 1, No. 5, Aug. 2007, pp. 190-192.XP055036995.

Shubeita, "Near-field optical microscopy of strongly scattering microporous metal/polymer membranes", Optics Communications, Mar. 2003, vol. 217, No. 1-6, pp. 23-30.

Vollprecht, "Quantification of Quaternary Mixtures of Low Alcohols in Water: Temporal-Resolved Measurements with Microporous and Hyperbranched Polymer Sensors for Reduction of Sensor Number", Analytical Chemistry, Sep. 2005, vol. 77, No. 17, pp. 5542-5550.

International Search Report for PCT International Application No. PCT/US2012/042233 mailed on Sep. 17, 2012, 5 pages.

* cited by examiner

SURFACE PLASMON RESONANCE SENSOR ELEMENT AND SENSOR INCLUDING THE SAME

FIELD

The present disclosure relates broadly to sensors, and more particularly to surface plasmon resonance sensors, and methods for their manufacture and use.

BACKGROUND

At an interface between two transparent media of different refractive index (e.g., glass and water), light coming from the side of higher refractive index is partly reflected and partly refracted. Above a certain critical angle of incidence, no light is refracted across the interface, and total internal reflection is observed. While incident light is totally reflected the electromagnetic field component penetrates a short (tens of nanometers (nm)) distance into a medium of a lower refractive index creating an exponentially attenuating evanescent wave. If the interface between the media is coated with a thin layer of metal (e.g., gold), and light is monochromatic and p-polarized (i.e., polarized parallel with respect to a plane on which the light is incident), the intensity of the reflected light is sharply reduced at a specific incident angle (called surface plasmon resonance (SPR)) due to the resonance energy transfer between the evanescent wave and surface plasmons. The resonance conditions are influenced by the material adsorbed onto the thin metal film.

Surface plasmons, also termed "surface plasmon polaritons", are surface electromagnetic waves that propagate in a direction parallel to a metal/dielectric (or metal/vacuum) interface. Since the wave is on the boundary of the metal and the dielectric, these oscillations are very sensitive to any change of this boundary, such as the adsorption of molecules to the metal surface. In one common configuration, termed the Kretschmann configuration, the thin metallic layer is disposed onto a transparent substrate (e.g., glass). Light illuminates the thin metallic layer through the transparent substrate, and an evanescent wave penetrates through the thin metallic layer. The plasmons are excited at the opposite side of the film thin metallic layer.

Surface plasmon resonance spectroscopy has been used as an analytical technique in various biological applications wherein a molecule is bound to a receptor attached to the metal layer. Surface plasmon resonance spectroscopy has also been used to detect organic vapors. For example, the use of MAKROLON M2400 polycarbonate from Bayer MaterialScience AG, Leverkusen, Germany) as a dielectric layer for use in SPR has been reported by Kieser et al. in *Analytical Chemistry*, 2002, vol. 74, pp. 4781-4787. MAKROLON polycarbonate is reported therein as being a microporous glassy polymer and having a mean size of the pores of 0.1 $nm^3$.

SUMMARY

In a first aspect, the present disclosure provides a surface plasmon resonance sensor element comprising:
 a thin metallic layer;
 an optical construction disposed on the thin metallic layer for directing light to and away from the thin metallic layer;
 an absorptive layer disposed on the thin metallic layer opposite the optical construction, the absorptive layer comprising a polymer of intrinsic microporosity having an average pore volume of at least 0.4 cubic nanometers ($nm^3$).

In a second aspect, the present disclosure provides a surface plasmon resonance sensor comprising:
 a source of plane polarized light;
 a surface plasmon resonance sensor element according to the present disclosure;
 a vapor delivery chamber comprising an inlet port, an outlet port, and a sampling port, wherein the sampling port and at least a portion of the absorptive layer are hermetically sealed together;
 a detector for detecting an image corresponding to a minimal intensity of light reflected from the thin metallic layer, thereby measuring a resonance angle.

Advantageously, SPR sensor elements according to the present disclosure, and SPR sensors including them, have increased sensitivity for analyte vapors as compared to previous SPR sensors (e.g., those using MAKROLON-type polycarbonate).

As used herein:
The term "absorptive" and "absorption" in reference to the absorptive layer include both absorption and adsorption; and
The term "monomeric unit" refers to a recurring group of atoms present in the structure of a polymer, including the polymer backbone, and corresponding to a single monomer molecule (whether actual or theoretical). A polymer (exclusive of end groups) may consist of one or more different monomeric units.

The features and advantages of the present disclosure will be further understood upon consideration of the detailed description as well as the appended claims.

In all cases, the disclosure is presented by way of representation and not limitation. It should be understood that numerous other modifications and embodiments can be devised by those skilled in the art, which fall within the scope and spirit of the principles of the disclosure. The figures may not be drawn to scale. Like reference numbers may have been used throughout the figures to denote like parts.

DETAILED DESCRIPTION

Figure 1:
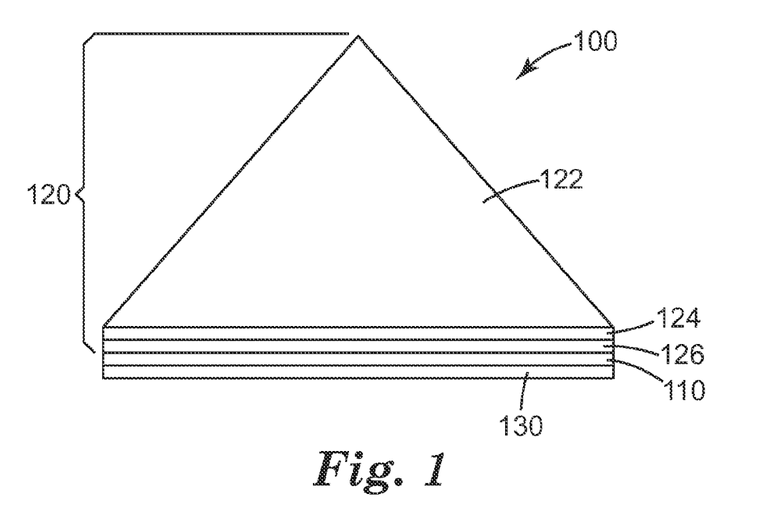
FIG. 1 is a schematic cross-sectional view of an exemplary SPR sensor element according to the present disclosure.

Referring now to FIG. 1, exemplary SPR sensor element 100 comprises thin metallic layer 110, optical construction 120, and absorptive layer 130. Optical construction 120 is disposed on thin metallic layer 110 and serves to directing light to and away from thin metallic layer 110. Optical construction 120 comprises optical prism 122, transparent plate 126, and transparent fluid 124 sandwiched therebetween. Optical prism 122, transparent plate 126, and transparent fluid 124 have substantially the same (i.e., matched) indexes of refraction. Absorptive layer 130 is disposed on thin metallic layer 110 opposite optical construction 120. Absorptive layer 130 comprises a polymer of intrinsic microporosity having an average pore volume of at least 0.4 $nm^3$.

The thin metallic layer typically comprises a metal such as, for example, gold, silver, aluminum, or copper, although other metals (e.g., titanium or chromium) may be used if desired. Combinations of metals may also be used. In some embodiments, the combination of metals comprises a bilayer construction wherein a metal layer furthest from the optical construction comprises a metal such as, for example, gold, copper, or silver and contacts a tie layer (in contact with the optical construction) which comprises a metal or metal-containing compound such as, for example, titanium, chromium, nickel, copper, cobalt, molybdenum, tantalum nitride, or an alloy thereof. The thickness of the thin metallic layer should be sufficiently thin that is less than the effective length of the evanescent wave. Typically, thicknesses of the thin metallic layer in a range of from about from 10 nm to about 100 nm may be effective, although other thicknesses may be used. The metal layer may be deposited according to any suitable technique, including, for example, thermal vapor deposition and sputtering techniques.

The optical construction directs light to and away from the thin metallic layer. The optical construction may be a unitary body or an assemblage of component parts. For example, the optical construction may be an optical prism (e.g., a triangular prism or a cylindrical lens), or it may be a combination of optical elements (e.g., as shown in FIG. 1).

The absorptive layer comprises a polymer of intrinsic microporosity (PIM) having an average pore volume of at least 0.4 nm$^3$. In some embodiments, the PIM has an average pore volume of at least 0.45 nm$^3$. Pore volume may be determined by positron annihilation lifetime spectroscopy (PALS); for example, as described by de Miranda et al. in *Physical Status Solidi RRL,* 2007, vol. 1, No. 5, pp. 190-192.

PIMs tend to pack poorly causing intrinsic porosity (void spaces) on the order of two nm or less that cannot be eliminated. Such polymers can be prepared by step-growth polymerization where at least one bis-catechol (A) is allowed to react with at least one fluorinated arene (B) under basic conditions as shown in Scheme I (below) according to the procedure reported by Budd et al. in *Chemical Communications,* 2004, (2), pp. 230-231.

SCHEME 1

Due to the rigidity and contorted nature of the backbone of the resulting polymers, these polymers are unable to pack tightly in the solid state and thus have at least 10 percent free volume and are intrinsically microporous.

In some embodiments, the PIM may be a homopolymer having a monomeric unit selected from the group consisting of Monomeric unit A and Monomeric Unit B which homopolymers respectively correspond to PIM-1 and PIM-7 in de Miranda et al., *Physical Status Solidi RRL,* 2007, vol. 1, No. 5, pp. 190-192, which reports that PIM-1 and PIM-7 at room temperature have an average radius (i.e., average pore radius) of 0.48 nm and an average volume (i.e., average pore volume) of 0.47 nm$^3$ as determined by positron annihilation lifetime spectroscopy (PALS).

PIM homopolymers having monomeric unit A can be formed by step-growth polymerization as described by Budd et al. in *Advanced Materials,* 2004, vol. 16, No. 5, pp. 456-459. PIM homopolymers having monomeric unit B can be formed according to the method described by Budd et al. in *Journal of Membrane Science,* 2005, vol. 251, pp. 263-269.

The absorptive layer may be deposited by any suitable technique. One useful technique involves spin coating a solution of the PIM material in a suitable solvent, for example, as shown in the examples hereinbelow. The absorptive layer may comprise one or more additional components such as, for example, antioxidants, fillers, residual solvent, wetting aids, leveling agents. The thickness of the absorptive layer is typically in a range of from 0.1 micron to 10 microns, although other thickness may also be used.

Figure 2:
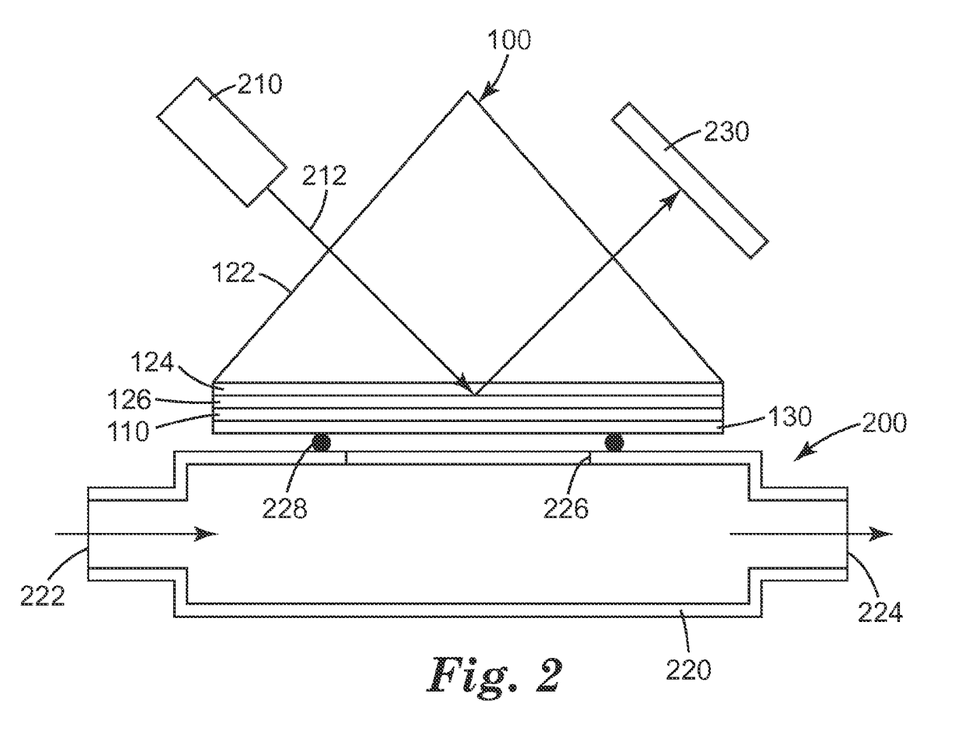
FIG. 2 is a schematic cross-sectional view of an exemplary SPR sensor according to the present disclosure.

SPR sensor elements according to the present disclosure are useful in SPR sensors. Referring now to FIG. 2, exemplary SPR sensor 200 comprises source of p-polarized light 210, SPR sensor element 100, vapor delivery chamber 220, and detector 230. SPR sensor element 100 may optionally be located on a rotation stage (not shown) in order to control the incident angle of light.

Source of p-polarized light 210 provides light that is p-polarized (i.e., electric field component is polarized in the same plane as the incident ray and the surface normal of the thin metallic layer). This may be accomplished using a light source such as a laser, or a collimated white light source in combination with a polarizer and optional collection optics. The use of a collimated white light source is generally more desirable than a laser due to interference fringes that may result in the resultant SPR image. The polarizer is used to select p-polarized light, and the optional collection optics (used with white light sources) consist of a narrow band pass filter, typically centered in the near-infrared region, that is used to select the excitation wavelength for the experiment. SPR sensor element 100 is arranged such that p-polarized light is incident on the thin metallic layer.

Vapor delivery chamber 220 comprises inlet port 222, outlet port 224 and sampling port 226. Sampling port 226 and at least a portion of the absorptive layer 130 are hermetically sealed together using o-ring 228. In typical use, analyte vapor to be analyzed is introduced into vapor delivery chamber 220 through inlet port 222. Vapor delivery chamber 220 may be made of any gas impermeable material such as for example metal, glass, or plastic.

Typically, the analyte vapor comprises a volatile organic compound; however, this is not a requirement. Examples of suitable analyte vapors include aliphatic hydrocarbons (e.g., n-octane or cyclohexane), ketones (e.g., acetone or methyl ethyl ketone), aromatic hydrocarbons (benzene, toluene, chlorobenzene, or naphthalene), nitriles (e.g., acetonitrile or benzonitrile), chlorinated aliphatic hydrocarbons (e.g., chloroform, dichloroethane, methylene chloride, carbon tetrachloride, or tetrachloroethylene), esters 5 (e.g., vinyl acetate, ethyl acetate, butyl acetate, or methyl benzoate), sulfides (e.g., phenyl mercaptan), ethers (e.g., methyl isobutyl ether or diethyl ether, aldehydes (e.g., formaldehyde, benzaldehyde, or acetaldehyde), alcohols (e.g., methanol or ethanol), amines (e.g., 2-aminopyridine), organic acids (e.g., acetic acid, propanoic acid), isocyanates (e.g., methyl isocyanate or toluene-2,4-diisocyanate), and nitro-substituted organics (e.g., nitromethane or nitrobenzene).

Detector 230 detects an image corresponding to a minimum intensity of light reflected from the thin metallic layer, thereby measuring a resonance angle. Depending on the amount of analyte vapor absorbed by the absorptive layer, its dielectric constant will change resulting a corresponding change in the angle of reflected light. The detector response can be correlated to the concentration of analyte vapor present in the vapor delivery chamber. Suitable detectors include, for example, photomultiplier tubes, photodiodes, photoconductors, phototransistors, and charge-coupled detectors (CCDs). For example, a linear CCD array may be used.

If desired, the sensor element may be heated to an elevated temperature (e.g., in a range of from 50° C. to 70° C.). This may lessen humidity effects in the sensor element response.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.
Preparation of PIM Material (PIM-1)

PIM-1 (a Polymer of Intrinsic Microporosity) was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 5,5',6,6'-Tetrahydroxy-3,3,3',3'-tetramethyl-1,1'-spirobisindane (40.000 grams (g)) was combined with 23.724 g of tetrafluoroterephthalonitrile, 97.373 g potassium carbonate, and 1016.8 g of N,N-dimethylformamide, and the mixture was heated at 68° C. for 72 hours. The resultant mixture was poured into water, and the precipitate was isolated by vacuum filtration. The resulting material was twice dissolved in tetrahydrofuran, precipitated from methanol, and air dried at room temperature. The dried PIM-1 polymer was a solid yellow product obtained having a number-average molecular weight of approximately 41,900 grams/mole as determined by gel permeation chromatography analysis using light scattering detection.
Preparation of Glass Slides for Sensor Element Glass slides (glass number 0050-0050-0010-GF-CA, 50 mm×50 mm, 1.1 mm thick, material C-263, surface 80/50, from Precision Glass & Optics, Santa Ana, Calif.) were cleaned by soaking for 30-60 minutes in ALCONOX LIQUI-NOX detergent solution from Alconox, Inc., White Plains, N.Y., then scrubbing each side of the slides with a bristle brush, rinsing under warm tap water followed by a final rinse with deionized water. The slides were allowed to air dry covered to prevent dust accumulation on the surface. The dry, clean slides were stored in 3-inch (7.6-cm) wafer carriers from Entegris, Chaska, Minn.
Surface Plasmon Resonance Sensor A surface plasmon resonance sensor was set up as generally shown in FIG. 2. The sensor element was mounted on a prism (N-BK7 uncoated prism, stock No. NT32-549, from Edmund Optics, Barrington, N.J.) using a drop of index matching oil (series A, $n_D$ at 25° C.=1.560±0.0002, from Cargille-Sacher Laboratories, Inc., Cedar Grove, N.J.). The SPR sensor mounted prism was attached to a VOC delivery chamber using an o-ring, a sensor holder, and screws. The monochromic radiation source was a p-polarized He—Ne laser (632.8 nm, obtained from Uniphase, Milpitas, Calif.) with a laser power source (model 1201-1 from Uniphase). Since the high intensity of laser source causes the saturation of detection signals, a filter (FSR-OD 300 absorptive ND filter, 25.4 mm DIA, 3.0 OD at 546.1 nm obtained from Newport Corp. of Irvine, Calif.) was placed in the front of the laser. In order to obtain the reflection with wide range of angles without rotating the sensor holder, a lens (DIN 60, numerical aperture=0.85, obtained from Edmund optics of Barrington, N.J.) was placed between the laser and the sensor element holder. In order to locate positions of the reflection minimum, a linear 128-pixel CCD array (model TSL1401R, obtained from TAOS of Plano, Tex.) with a power supply (model 6212A, obtained from Hewett Packard of Palo Alto, Calif.) was used. The pixels measure 63.5 micrometers (Height) by 55.5 micrometers (Width) with 63.5 micrometers center-to-center spacing and 8 micrometers spacing between pixels. The total length of CCD array was 0.813 centimeters for 128 pixels. The CCD array was mounted on the evaluation module (model PC404A, obtained from TAOS, Plano, Tex.) and the module was attached to a 3-way transitional stage (obtained from Line Tool, Allentown, Pa.). The distance between the gold/polymer sensing layer and CCD array was 2.25 centimeters and the CCD array was perpendicularly oriented to the reflected radiation. A digital camera was used to take images of the instrumental setup and the incident radiation angles were measured analyzing the digital camera images. The signals from the evaluation module were acquired by an oscilloscope (model TDS 3024B, obtained from Tektronix, Beaverton, Oreg.). A customized Labview program was used to interface with the Tektronix oscilloscope for data acquisition. The positions of reflection minimum were calculated using a peak/valley finder algorithm built in Labview (software available from National Instruments, Austin, Tex.) program.

All tests were performed in air that had been passed over DRIERITE desiccant (from W. A. Hammond Drierite Co. Ltd., Xenia, Ohio) to remove moisture, and passed over activated carbon to eliminate any organic contaminates. Vapor tests were conducted using a 10 L/minute dry air flow through the system. VOC levels were generated using a KD Scientific syringe pump (available from KD Scientific Inc., Holliston, Mass.) fitted with a one-milliliter gas-tight syringe (obtained from Hamilton Company, Reno, Nev.). The syringe pump delivered a VOC solvent onto a piece of filter paper suspended in a 500-mL three necked flask. The flow of dry air passed over the paper and vaporized the solvent. Delivering the solvent at different rates by controlling the syringe pump generated different concentrations of vapor. The syringe pump was controlled by a LABVIEW program that allowed VOC profiles to be generated during a test run. A MIRAN IR analyzer (from Thermo Fischer Scientific, Inc., Waltham, Mass.) was used to verify the set concentrations. All measurements were done at room temperature.

Three different solvents were evaluated: toluene, ethanol, and methyl ethyl ketone (MEK), all from Sigma-Aldrich, Milwaukee, Wis.

Example 1

A 30.0 nm thick gold layer was coated onto a clean glass slide by thermal vapor deposition of gold at a rate of 0.1 nm per second (nm/sec). The deposition process was controlled using an Inficon XTC/2 thin film deposition controller from Inficon, East Syracuse, N.Y.

A 5.5 percent by weight PIM solution was prepared by combining the PIM-1 polymer with chlorobenzene in a small jar and mixing on a roller mill (Mini Bottle Roller number 348920 from Wheaton Science Products, Millville, N.J.) for about 4 hours. The solution was then filtered through a one-micron filter (ACRODISC 25 mm syringe filter with a one-micron glass fiber membrane from Pall Corp., Port Washington, N.Y.) and allowed to sit overnight to allow air bubbles to escape.

The gold surface of slide was spin coated with the PIM-1 solution using a Model WS 400B-8NPP/LITE spin coater from Laurell Technologies Corporation of North Wales, Pa. The PIM solution was dispensed to the slide for 15 sec at 300 rpm, and then coated for 45 sec at 2000 rpm. The thickness of the PIM layer was 620 nm. The thickness was measured by removing a small section of the coating an acetone soaked cotton swab and measuring on a Model XP-1 Profilometer from Ambios Technology, Santa Cruz, Calif. The parameters used in the measurement were a scan speed of 0.1 mm/sec, a scan length of 5 mm, a range of 10 micrometers, a stylus force of 0.20 mg and a filter level of 4. After measuring, the coated slides were baked for 1 hour at 100° C.

Individual sensor elements were prepared by dicing the coated slide using a standard glass scoring cutter into four 25 mm by 25 mm elements. The slide was cut on the back (inactive side) while supporting the front (active) surface to prevent damage to it. After dicing into individual sensor elements, the sensor elements were stored in 1.5-inch (3.8-cm) wafer holders from Entegris, Chaska, Minn.

The sensor element was mounted in a SPR SENSOR apparatus as described above. The incident radiation angle under dry air was 63.5 degrees. The sensor was exposed to a series of toluene concentrations of toluene concentrations (i.e., 3, 6, 9, 12 ppm of toluene in dry air).

Figure 3:
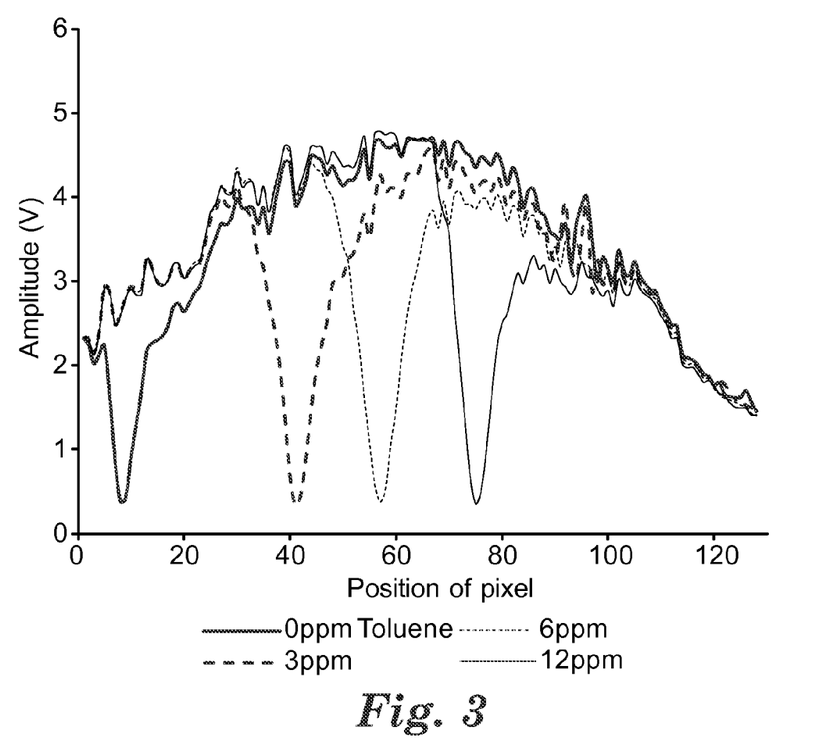
FIG. 3 is a plot of reflected light amplitude versus pixel location of a CCD array for various toluene vapor concentrations from Example 1.

FIG. 3 reports the signals obtained from CCD array. A higher pixel position represents reflected radiation at higher angles. Without toluene exposure (0 ppm toluene), a clear reflection minimum (valley) was observed. Upon exposure to toluene, the location of the reflection minimum shifted to higher pixel position.

Figure 4:
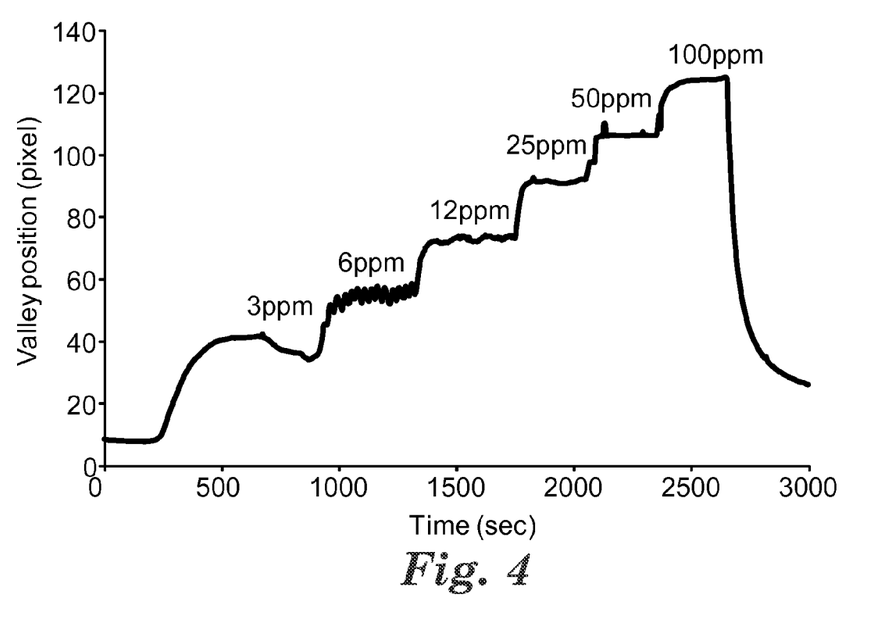
FIG. 4 is a plot of reflected light valley positions in pixels of a CCD array versus various toluene vapor concentrations from Example 1.

FIG. 4 reports the valley position change after a series of toluene exposure with respect to time. Clear steps of the valley position changes are observed at each stepped concentration. Some fluctuation of signals comes from the fluctuating toluene vapor delivery caused by the syringe pump. The fluctuation gives insight to the response time of the SPR sensors. The SPR sensor can spontaneously respond to spontaneously fluctuating VOC concentrations in seconds.

Example 2

A sensor element was prepared according to the procedure described in Example 1, except that two metal layers were coated on a slide and a 3.6 percent by weight solids PIM-1 solution was used. A 5.0 nm thick layer of titanium was deposited on the PGO slide at a rate of 0.1 nm/sec followed by depositing a 30.0 nm layer of gold at rate of 0.5 nm/sec over the titanium layer.

A 3.6 percent by weight PIM-1 solution in chlorobenzene (prepared generally as described in Example 1) was dispensed to the sensor for 15 sec at 300 rpm, and then coated for 45 sec at 4000 rpm. The thickness of PIM-1 layer was 203 nm. The radiation angle under dry air was 51.5 degrees. Sensor elements were individually mounted in a SPR SENSOR apparatus as described above.

Each sensor element was tested using ethanol, methyl ethyl ketone (MEK), or toluene. Results are reported in Tables 1, 2, and 3.

Comparative Example C1

A sensor was prepared according to the procedure of Example 2, except that a 1.7 percent polycarbonate ((poly (bisphenol A carbonate) polycarbonate from Sigma Aldrich of Milwaukee, Wis., and corresponding to MAKROLON polycarbonates, used without further purification) solution in chloroform was dispensed to the slide for 5 sec at 300 rpm and then coated for 40 sec at 3000 rpm. The thickness of polycarbonate layer was 221 nm. Sensor elements were tested with ethanol, MEK, and toluene described in Example 2. The radiation angle under dry air was 61.5 degrees. Results are reported in Tables 1, 2, and 3.

TABLE 1

| CONCENTRATION OF | SHIFT OF VALLEY POSITION, pixels | |
|---|---|---|
| ETHANOL, ppm | EXAMPLE 2 | EXAMPLE C1 |
| 0 | 0.00 | 0.00 |
| 15 | 0.76 | 0.03 |
| 30 | 1.41 | 0.06 |
| 60 | 2.54 | 0.11 |
| 125 | 4.50 | 0.34 |
| 250 | 6.35 | 0.57 |
| 500 | 9.27 | 0.84 |
| 1000 | 12.09 | 1.24 |

TABLE 2

| CONCENTRATION OF | SHIFT OF VALLEY POSITION, pixels | |
|---|---|---|
| MEK, ppm | EXAMPLE 2 | EXAMPLE C1 |
| 0 | 0.00 | 0.00 |
| 15 | 8.11 | 0.48 |
| 30 | 10.36 | 0.70 |
| 60 | 12.88 | 0.97 |
| 125 | 15.76 | 1.35 |
| 250 | 19.03 | 1.83 |
| 400 | 23.75 | 2.32 |
| 500 | 25.48 | 2.59 |
| 1000 | 30.48 | 3.55 |

TABLE 3

| CONCENTRATION OF | SHIFT OF VALLEY POSITION, pixels | |
|---|---|---|
| TOLUENE, ppm | EXAMPLE 2 | EXAMPLE C1 |
| 0 | 0.00 | 0.00 |
| 3 | 30.33 | 0.39 |
| 6 | 40.46 | 0.51 |
| 12 | 54.67 | 0.71 |
| 25 | 65.88 | 1.05 |
| 50 | 76.81 | 1.42 |
| 100 | 89.02 | 2.16 |
| 200 | 102.60 | 3.10 |

SELECT EMBODIMENTS OF THE DISCLOSURE

In a first embodiment, the present disclosure provides a surface plasmon resonance sensor element comprising:
a thin metallic layer;
an optical construction disposed on the thin metallic layer for directing light to and away from the thin metallic layer;
an absorptive layer disposed on the thin metallic layer opposite the optical construction, the absorptive layer comprising a polymer of intrinsic microporosity having an average pore volume of at least 0.4 cubic nanometers.

In a second embodiment, the present disclosure provides a surface plasmon resonance sensor element according to the first embodiment, wherein the optical construction consists of a prism.

In a third embodiment, the present disclosure provides a surface plasmon resonance sensor element according to the first or second embodiment, wherein the optical construction comprises a prism, a transparent plate, and a fluid sandwiched therebetween, wherein the prism, transparent plate, and fluid have matched indexes of refraction.

In a fourth embodiment, the present disclosure provides a surface plasmon resonance sensor element according to any one of the first to third embodiments, wherein the polymer of intrinsic microporosity has an average pore volume of at least 0.45 cubic nanometers.

In a fifth embodiment, the present disclosure provides a surface plasmon resonance sensor element according to any one of the first to fourth embodiments, wherein the polymer of intrinsic microporosity is a homopolymer having a monomeric unit selected from the group consisting of and In a sixth embodiment, the present disclosure provides a surface plasmon resonance sensor element according to any one of the first to fifth embodiments, wherein the thin metallic layer comprises at least one of gold, silver, aluminum, or copper.

In a seventh embodiment, the present disclosure provides a surface plasmon resonance sensor comprising:
a source of p-polarized light;
a surface plasmon resonance sensor element according to any of the first to seventh embodiments;
a detector for detecting an image corresponding to a minimal intensity of light reflected from the thin metallic layer, thereby measuring a resonance angle.

In an eighth embodiment, the present disclosure provides a surface plasmon resonance sensor according to the seventh embodiment, wherein the source of p-polarized light comprises a laser.

In a ninth embodiment, the present disclosure provides a surface plasmon resonance sensor according to the seventh or eighth embodiment, wherein the detector comprises a photodiode array.

In a tenth embodiment, the present disclosure provides a surface plasmon resonance sensor according to any one of the seventh to ninth embodiments, wherein the optical construction consists of a prism.

In an eleventh embodiment, the present disclosure provides a surface plasmon resonance sensor according to any one of the seventh to ninth embodiments, wherein the optical construction comprises a prism, a transparent plate, and a fluid sandwiched therebetween, wherein the prism, transparent plate, and fluid have matched indexes of refraction.

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A surface plasmon resonance sensor element comprising:
    a thin metallic layer;
    an optical construction disposed on the thin metallic layer for directing light to and away from the thin metallic layer;
    an absorptive layer disposed on the thin metallic layer opposite the optical construction, the absorptive layer comprising a polymer of intrinsic microporosity having an average pore volume of at least 0.4 cubic nanometers.

2. A surface plasmon resonance sensor element according to claim 1, wherein the optical construction consists of a prism.

3. A surface plasmon resonance sensor element according to claim 1, wherein the optical construction comprises a prism, a transparent plate, and a fluid sandwiched therebetween, wherein the prism, transparent plate, and fluid have matched indexes of refraction.

4. A surface plasmon resonance sensor element according to claim 1, wherein the polymer of intrinsic microporosity has an average pore volume of at least 0.45 cubic nanometers.

5. A surface plasmon resonance sensor element according to claim 1, wherein the polymer of intrinsic microporosity is a homopolymer having a monomeric unit selected from the group consisting of and 6. A surface plasmon resonance sensor element according to claim 1, wherein the thin metallic layer comprises at least one of gold, silver, aluminum, or copper.

7. A surface plasmon resonance sensor comprising:
    a source of p-polarized light;
    a surface plasmon resonance sensor element according to claim 1;
    a detector for detecting an image corresponding to a minimal intensity of light reflected from the thin metallic layer, thereby measuring a resonance angle.

8. A surface plasmon resonance sensor according to claim 7, wherein the source of p-polarized light comprises a laser.

9. A surface plasmon resonance sensor according to claim 7, wherein the detector comprises a photodiode array.

10. A surface plasmon resonance sensor according to claim 7, wherein the optical construction consists of a prism.

11. A surface plasmon resonance sensor according to claim 7, wherein the optical construction comprises a prism, a transparent plate, and a fluid sandwiched therebetween, wherein the prism, transparent plate, and fluid have matched indexes of refraction.

12. A surface plasmon resonance sensor element according to claim 7, wherein the polymer of intrinsic microporosity has an average pore volume of at least 0.45 cubic nanometers.

13. A surface plasmon resonance sensor element according to claim 7, wherein the polymer of intrinsic microporosity is a homopolymer having a monomeric unit selected from the group consisting of 14. A surface plasmon resonance sensor according to claim 7, wherein the thin metallic layer comprises at least one of gold, silver, or copper.

15. The surface plasmon resonance sensor element according to claim 1, wherein the absorptive layer has a thickness of 0.1 micron to 10 microns.

16. The surface plasmon resonance sensor element according to claim 1, wherein the absorptive layer is capable of absorbing a vapor, and has a dielectric constant that is changeable depending on the amount of the absorbed vapor.

17. The surface plasmon resonance sensor element according to claim 1, wherein the polymer of intrinsic microporosity has at least 10% free volume.

18. The surface plasmon resonance sensor element according to claim 1, wherein the absorptive layer is formed by spin coating a solution of the polymer on a surface of the thin metallic layer to form a metal/dielectric interface.

* * * * *